US007800755B1

(12) United States Patent
Poirier et al.

(10) Patent No.: US 7,800,755 B1
(45) Date of Patent: Sep. 21, 2010

(54) HIGH-SPEED POLARIMETER HAVING A MULTI-WAVELENGTH SOURCE

(75) Inventors: Peter M. Poirier, San Diego, CA (US); Michael G. Lovern, Spring Valley, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 592 days.

(21) Appl. No.: 11/772,364

(22) Filed: Jul. 2, 2007

(51) Int. Cl.
*G01J 4/00* (2006.01)

(52) U.S. Cl. ..................... 356/367; 356/369

(58) Field of Classification Search ......... 356/364–367, 356/369
See application file for complete search history.

(56) References Cited

U.S. PATENT DOCUMENTS

| | | | |
|---|---|---|---|
| 4,306,809 A | 12/1981 | Azzam | |
| 4,681,450 A | 7/1987 | Azzam | |
| 5,045,701 A | 9/1991 | Goldstein et al. | |
| 5,081,348 A | 1/1992 | Siddiqui | |
| 5,247,176 A | 9/1993 | Goldstein | |
| 5,548,404 A | 8/1996 | Kupershmidt et al. | |
| 5,757,671 A | 5/1998 | Drevillon et al. | |
| 5,859,424 A * | 1/1999 | Norton et al. | 250/226 |
| 5,956,147 A | 9/1999 | Jellison, Jr. et al. | |
| 6,184,984 B1 * | 2/2001 | Lee et al. | 356/369 |
| 6,275,291 B1 | 8/2001 | Abraham et al. | |
| 6,384,916 B1 * | 5/2002 | Furtak | 356/369 |
| 6,630,658 B1 * | 10/2003 | Bohnert et al. | 250/227.14 |
| 7,064,828 B1 * | 6/2006 | Rovira et al. | 356/369 |
| 7,245,376 B2 * | 7/2007 | Liphardt et al. | 356/369 |
| 2002/0008874 A1 * | 1/2002 | Lee et al. | 356/369 |
| 2003/0223064 A1 * | 12/2003 | Anderson et al. | 356/364 |
| 2005/0002017 A1 * | 1/2005 | Haran | 356/73.1 |
| 2005/0264813 A1 * | 12/2005 | Giakos | 356/369 |

OTHER PUBLICATIONS

Clemenceau, Breugnot, and Collot, "Polarization Diversity Active Imaging", Proc. SPIE, vol. 3380, pp. 284-291 (1998).
Meier and Priest, "Mueller Matrix Measurements of Black and White Materials in the Infrared", Proc. SPIE, vol. 4133, pp. 82-91 (2000).
Gerligand, Chipman, Sornsin, and Smith, "Polarization Signatures of Spherical and Conical Targets Measured by Mueller Matrix Imaging Polarimetry", Proc. SPIE, vol. 3121, pp. 63-73 (1997).

(Continued)

*Primary Examiner*—Tarifur Chowdhury
*Assistant Examiner*—Michael LaPage
(74) *Attorney, Agent, or Firm*—Ryan J. Friedl; Kyle Eppele (57) ABSTRACT

A polarimeter includes a multi-wavelength source for generating electromagnetic waves having at least two different wavelengths, means for separating electromagnetic waves, the electromagnetic waves including electromagnetic waves generated by the multi-wavelength source and electromagnetic waves received from a sample contacted by the electromagnetic waves generated by the multi-wavelength source, a fixed waveplate, wherein the fixed waveplate is configured to convert one polarization state to multiple polarization states that allow for calculations of linear and circular polarization components of the electromagnetic waves, a free space coupler, a beam splitter, and more than one detector. The polarimeter may be used in a method for high-speed measurement of linear and circular polarization components of electromagnetic waves.

11 Claims, 8 Drawing Sheets

OTHER PUBLICATIONS

Lewis, Jordan, and Jakeman, "Backscatter Linear and Circular Polarization Analysis of Roughened Aluminum", Applied Optics, vol. 37, No. 25, pp. 5985-5992 (1998).

Haner, McGuckin, and Bruegge, "Polarization Characteristics of Spectralon Illuminated by Coherent Light", Applied Optics, vol. 38, No. 30, pp. 6350-6356 (1999).

Gamiz, Victor L., "Performance of a Four Channel Polarimeter With Low Light Level Detection", Proc. SPIE, vol. 3121, pp. 35-46 (1997).

Schwiecker, Dang, Thanh, Zilian, Schneider, and Heland, "High-Speed Ellipsometry for the Production of Thin Metal Layers", Proc. SPIE, vol. 1746, pp. 222-230 (1992).

Locke, Sabatke, Dereniak, Descour, Garcia, Hamilton, and McMillan, "Snapshot Imaging Spectropolarimeter", Proc. SPIE, vol. 4481, pp. 64-72 (2002).

Fetrow, Sposato, Bishop, and Caudill, "Spectral Polarization Signatures of Materials in the LWIR", Proc. SPIE, vol. 4133, pp. 249-260 (2000).

* cited by examiner

HIGH-SPEED POLARIMETER HAVING A MULTI-WAVELENGTH SOURCE

BACKGROUND OF THE INVENTION

The present invention is generally related to the field of polarimetry. Measurements of the properties of samples and a medium can be greatly enhanced by taking advantage of the polarization characteristics of electromagnetic radiation. Properties such as diattenuation, retardation, and depolarization can be determined from several polarization measurements. Knowledge of these properties can be useful for a variety of applications where other measured properties do not adequately characterize the sample and medium, such as the extent to which a sample depolarizes radiation.

A polarimeter is a device that measures polarization properties of radiation or the changes of those properties due to propagation through a medium, reflection from a sample, or both. A passive polarimeter measures the polarization state of the incoming radiation. An active polarimeter generates radiation with a controlled polarization state and analyzes the incoming polarization state. A complete polarimeter is one that can make all the measurements necessary to calculate all possible polarization characteristics. A complete passive polarimeter must be able to take a minimum of four measurements needed to calculate the four Stokes parameters and is sometimes referred to as a Stokes polarimeter. A complete active polarimeter must generate four independent polarization states and analyze the Stokes parameters for each generated state. Therefore, a complete active polarimeter must make a minimum of sixteen measurements. Such polarimeters are often complex and do not perform calculations with maximum speed.

Therefore, there is a current need for a high-speed polarimeter of minimal complexity that requires a minimal number of polarization measurements to calculate the linear and circular components necessary to determine the linear and circular characteristics of a sample or medium.

DETAILED DESCRIPTION OF SOME EMBODIMENTS

The term "polarization state" includes unpolarized, purely polarized, and partially polarized light. A state of polarization is typically described using the four Stokes parameters, $S_i$ ($i=0$ to 3). These parameters may be determined from measurements of the intensities of various polarization components, including linear horizontal (H), linear vertical (V), linear +45° (D), linear −45° (A), right circular (R), and left circular (L). The Stokes parameters may be described as follows:

$$S_0 = H+V \quad \text{(Eq. 1a)}$$

$$S_1 = H-V \quad \text{(Eq. 1b)}$$

$$S_2 = D-A \quad \text{(Eq. 1c)}$$

$$S_3 = R-L \quad \text{(Eq. 1d)}$$

The output Stokes parameters measured after the light passes through a medium or reflected from a sample or a combination of both may be described as $S_i'$ ($i=0$ to 3). The output parameters are a function of the initial Stokes parameters, $S_i$, and may be represented by a series of 4 equations with 16 coefficients. The functions may also be represented by four dimensional Stokes vectors containing $S_i$ and $S_i'$ values and a 4×4 Mueller matrix containing the following 16 coefficients:

$$S_0' = M_{00}S_0 + M_{01}S_1 + M_{02}S_2 + M_{03}S_3 \quad \text{(Eq. 2a)}$$

$$S_1' = M_{10}S_0 + M_{11}S_1 + M_{12}S_2 + M_{13}S_3 \quad \text{(Eq. 2b)}$$

$$S_2' = M_{20}S_0 + M_{21}S_1 + M_{22}S_2 + M_{23}S_3 \quad \text{(Eq. 2c)}$$

$$S_3' = M_{30}S_0 + M_{31}S_1 + M_{32}S_2 + M_{33}S_3 \quad \text{(Eq. 2d)}$$

$$\begin{pmatrix} S_0' \\ S_1' \\ S_2' \\ S_3' \end{pmatrix} = \begin{pmatrix} M_{00} & M_{01} & M_{02} & M_{03} \\ M_{10} & M_{11} & M_{12} & M_{13} \\ M_{20} & M_{21} & M_{22} & M_{23} \\ M_{30} & M_{31} & M_{32} & M_{33} \end{pmatrix} \begin{pmatrix} S_0 \\ S_1 \\ S_2 \\ S_3 \end{pmatrix}$$

The term "polarization component" means a characteristic of the electromagnetic wave which is dependent on the polarization state and may be measured by a radiometer with a polarizer placed in front of it. These components may be determined from measurements made of the intensity of the wave passing through linear horizontal, linear vertical, linear +45°, linear −45°, right circular, and left circular polarizers.

The term "co-polarized intensity measurement" means illuminating a sample with an incident beam of energy having a polarization state and measuring the transmitted or reflected intensity of the same polarization component of the incident polarization state. Circular components in transmission mode are reversed sense (e.g. right circular generation and left circular analyzed). An example of a co-polarized intensity measurement would be to illuminate a sample with a beam of linear vertical polarized light and measure the intensity of the reflected linear vertical polarized component.

The term "cross-polarized intensity measurement" means illuminating a sample with a beam of energy having a polarization state and measuring the transmitted or reflected intensity of a polarization component that is orthogonal to the polarization component of the incident polarization state. An example of a cross-polarized intensity measurement would be to illuminate a sample with a beam of linear vertical polarized light and measure the intensity of the reflected linear horizontal polarized component.

The term "depolarization" refers to the degree to which the polarization of a transmitted or reflected beam changes with respect to the incident beam. In terms of Mueller matrix elements, the depolarization may be defined as the degree of polarization, DOP, which may be defined as follows:

$$DOP = \sqrt{\frac{\left(\sum_{i=0}^{3}\sum_{j=0}^{3} M_{ij}^2\right) - M_{00}^2}{3 \cdot M_{00}^2}}$$ (Eq. 3)

and is calculated approximately as:

$$DOP \approx \frac{I_A - I_B}{I_A + I_B},$$ (Eq. 4)

where $I_A$ and $I_B$ are co-polarized intensity measurements and cross-polarized intensity measurements, respectively. For many samples this approximation is valid. For other samples the co-polarized and cross-polarized components for linear polarized light are significantly different than circular polarized light. In addition, the orientation of the linear polarized light often does not contribute to any significant changes (for example, little difference between vertical and +45° linear polarized co- and cross-polarized components). Therefore, a limited measurement of vertical and horizontal linear and circular co-polarized and cross-polarized components and subsequent calculation of vertical and horizontal linear and circular Mueller matrix elements (for example, $M_{00}$, $M_{01}$, $M_{03}$, $M_{10}$, $M_{30}$, $M_{11}$, and $M_{33}$) can adequately describe the polarization characteristics of a sample.

The term "diattenuation" means the property of an optical element or system whereby the intensity transmittance or reflectance of the exiting beam depends on the polarization state of the incident beam. The intensity transmittance or reflectance is a maximum $P_{max}$ for one incident state, and a minimum $P_{min}$ for the orthogonal state. The diattenuation may be defined as:

$$(P_{max}-P_{min})/(P_{max}-P_{min})$$ (Eq. 5)

In terms of Mueller matrix elements, the diattenuation, linear diattenuation, and circular diattenuation may be calculated as follows:

$$Dia = \sqrt{M_{01}^2 + M_{02}^2 + M_{03}^2}/M_{00}$$ (Eq. 6a)

$$LinDia = \sqrt{M_{01}^2 + M_{02}^2}/M_{00}$$ (Eq. 6b)

$$CirDia = M_{03}/M_{00}$$ (Eq. 6c)

The term "intensity" (I) means the time average of the square of the electric field amplitude.

The terms "polarimeter" and "active polarimeter" mean an instrument for the determination of the polarization state of an electromagnetic beam, or the polarization components of a sample illuminated with an electromagnetic beam of a controlled polarization state.

Figure 1:
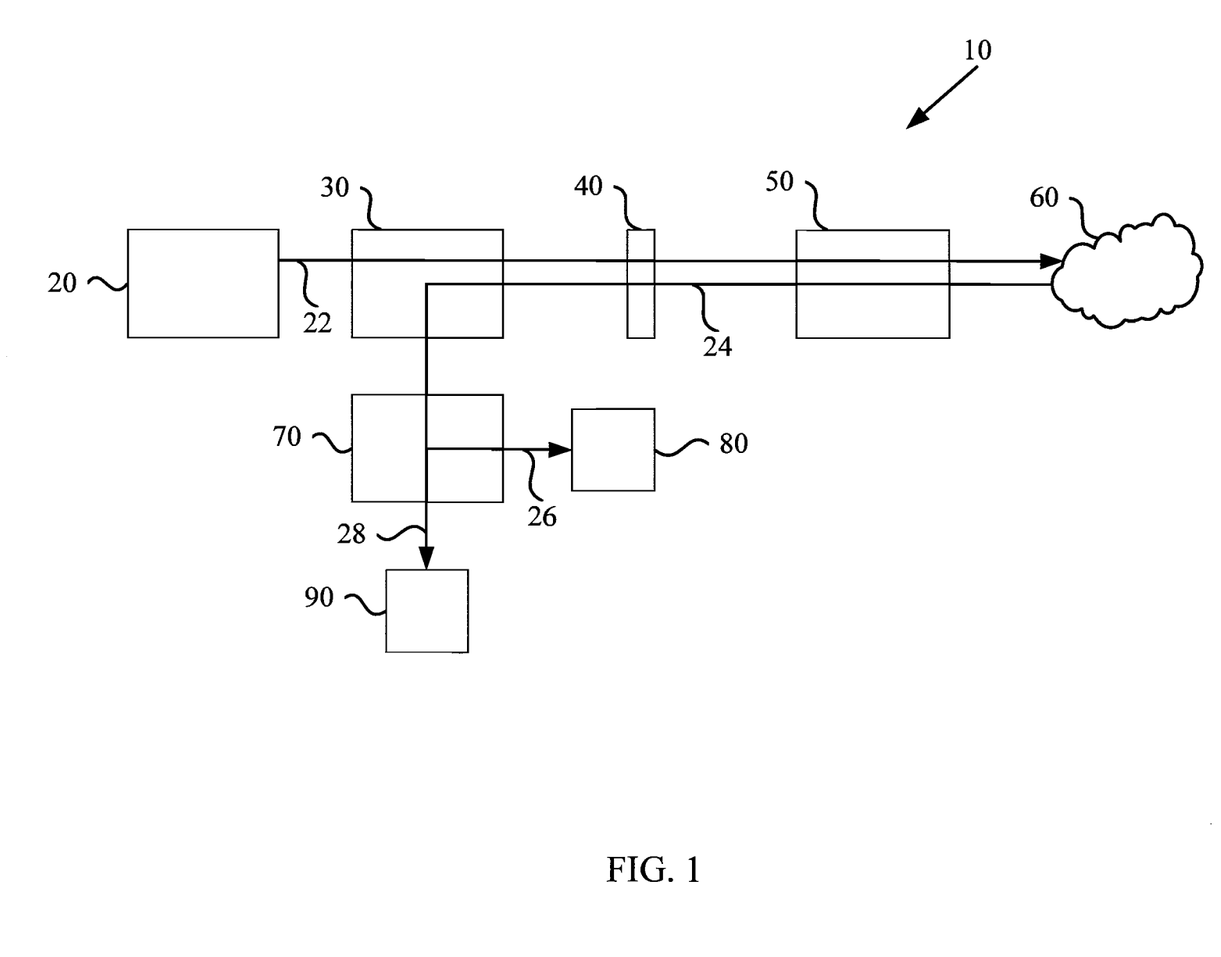
FIG. 1 shows a block diagram of an embodiment of a high-speed polarimeter with a monostatic reflection mode and having a multi-wavelength source.

FIG. 1 shows a block diagram of an embodiment of the high-speed polarimeter having a multi-wavelength source 10. Polarimeter 10 may have a monostatic reflective configuration, wherein polarimeter 10 may include a multi-wavelength source 20, an electromagnetic wave separator 30, a fixed waveplate 40, a free space coupler 50, a beam splitter 70, and detectors 80 and 90. Multi-wavelength source 20 may create an electromagnetic wave 22 that is transmitted to wave separator 30, fixed waveplate 40, free space coupler 50, and to a sample 60. The interaction of electromagnetic wave 22 with sample 60 may cause an electromagnetic wave 24 to be redirected back towards free space coupler 50, fixed waveplate 40, and electromagnetic wave separator 30. The polarization state of electromagnetic wave 24 may be the same as the electromagnetic wave 22, or it may be different, depending on the shape, angle, and surface material of sample 60. Sample 60 may comprise any type of material, in any shape or form. At wave separator 30, electromagnetic wave 24 may be directed to beam splitter 70. Beam splitter 70 may divide the orthogonal linear or circular components of electromagnetic wave 24, which may then be directed to detectors 80 and 90. As an example, vertical linear polarization component 26 may be directed to detector 80, which may be configured to detect vertical linear polarization components of electromagnetic waves, and horizontal linear polarization component 28 may be directed to detector 90, which may be configured to detect horizontal linear polarization components of electromagnetic waves.

In one embodiment, multi-wavelength source 20 may be a single radiation source having one output. Multi-wavelength source 20 may be operated in a continuous wave mode or pulsed wave mode. Multi-wavelength source 20 may also generate electromagnetic waves sequentially having multiple wavelengths. For example, in continuous wave mode for sequential wavelengths, multi-wavelength source 20 may generate sequential continuous electromagnetic waves each having a single wavelength, each wavelength having a single polarization state. As another example, in sequential pulsed wave mode, multi-wavelength source 20 may generate sequential pulsed electromagnetic waves each having a different wavelength, each wavelength having a single polarization state.

By way of example, multi-wavelength source 20 may generate electromagnetic waves 22 in the spectrums including, but not limited to: radio, infrared, visible, ultraviolet, and x-ray. The polarization state may include one or more different polarization components, which may be selected in response to previous measurements. Examples of multi-wavelength source 20 that may be suitable for use with polarimeter 10 may be commercially obtained from Thorlabs, model DFB1535-120 (operating around 1550 nm), Ando, model AQ4321A, and Intelite, model IS550-120.

In one embodiment, multi-wavelength source 20 may be a device that includes two or more radiation sources, such as laser diodes, combined with a coupling device (not shown). The coupling device may co-align the radiation sources so that the electromagnetic waves generated from each radiation source pass through the same components within polarimeter 10. In this embodiment, each radiation source of multi-wavelength source 20 may be operated in a continuous wave mode or pulsed wave mode and may generate electromagnetic waves sequentially having multiple wavelengths. For example, in the optical infrared spectrum, light from four laser diodes operating at 1450, 1500, 1550 and 1600 nanometer wavelengths, respectively, are each coupled into a fiber optic that is coupled into a wavelength division multiplexed (WDM) coupler. The WDM couples the light from all four radiation sources into a single fiber optic. The light from the fiber optic may be coupled into another fiber optic device or into bulk optics, such as a lens, and then into free space. In an embodiment having multiple radiation sources, multi-wavelength source 20 may include all necessary radiation coupling components necessary to co-align the beams. For example, fiber optic WDM couplers or bulk optics such as dichroic beam splitters or combiners may be used in the light sources. An array of radiation sources that are spatially separated and collimated may be combined if their beams overlap. However, the overlap of the beams must be such that the individual beam angles are within the tolerance of fixed waveplate 40.

Wave separator 30 may be operatively connected to multi-wavelength source 20. Wave separator 30 may serve to separate electromagnetic waves. The electromagnetic waves separated by wave separator 30 may include electromagnetic waves generated by multi-wavelength source 20 and transmitted to a sample, such as sample 60. The electromagnetic waves separated by wave separator 30 may also include electromagnetic waves received from a sample, such as sample 60. The electromagnetic waves received from a sample may include waves transmitted from the sample, or waves generated by multi-wavelength source 20 which contact the sample and are redirected back to wave separator 30. Examples of wave separator 30 include a directional coupler, such as a non-polarizing 50/50 beam splitter that may be obtained from Newport Corporation, as well as a fiber optic directional coupler or circulator, which may be commercially obtained from General Photonics.

Fixed waveplate 40 may be operatively connected to wave separator 30. Fixed waveplate 40 may be capable of converting one polarization state to multiple polarization states that allow for calculations of linear polarization components and circular polarization components of electromagnetic waves. As an example, fixed waveplate 40 may be an optical device that acts as a retarder, altering the polarization state of a light wave propagating through it. Fixed waveplate 40 may shift the phase of a light wave between two perpendicular polarization components. In one embodiment, fixed waveplate 40 may be a birefringent crystal with parallel surfaces and a specific thickness. As an example, the thickness of fixed quartz waveplate 40 may range from between 3 mm to 5 mm. The crystal may be cut such that there are two crystal axes (fast and slow) parallel to the surface of fixed waveplate 40. Light polarized along the fast axis may propagate faster than light polarized along the slow axis. Depending on the thickness of the crystal, light with polarization components along both axes may emerge in a different polarization state. An example of fixed waveplate 40 may be commercially obtained from the CVI or Newport corporations. Custom quartz waveplates, such as those having thicknesses of between 1 mm to 2 mm, may be commercially obtained from the Meadowlark Corporation.

Fixed waveplate 40 may be characterized by the amount of relative phase, $\delta$, that it impacts on the two components, which is related to the birefringence, $\Delta n(\lambda)$, and the thickness, t, of the crystal by the formula $$\delta = 2\pi \Delta n(\lambda) t/\lambda \quad \text{(Eq. 7)}$$

where $\lambda$ is the wavelength in a vacuum. As an example, in one embodiment fixed waveplate 40 may be a quarter waveplate. A quarter waveplate creates a quarter wavelength phase shift and may change linearly polarized light to circular polarized light, and vice versa. This may be accomplished by adjusting the orientation of the incident linear polarized light such that it makes a 45 degree angle with respect to the fast axis, providing equal amplitude fast and slow waves. As another example, fixed waveplate 40 may be a half waveplate. A half waveplate retards one polarization by a half wavelength, or 180 degrees ($\pi$ radians), rotating the polarization direction of linear polarized light. For example, a half waveplate oriented at a 45 degree angle between the incident linear polarization and the fast axis will result in a 90 degree rotation of the linear polarized light (vertical incident will be transmitted as horizontal, etc. . . . ).

A simple waveplate will impart a phase difference that depends on the wavelength of the light, due to the effects of dispersion. The thickness of fixed waveplate 40 may be chosen such that the retardance may range from full to three quarters of a wave, or $N2\pi$ to $N2\pi+(3/2)\pi$ radians ($N*360$ degrees to $N*360+270$ degrees, where N is an integer), over a range of wavelengths. Thus, the retardance may have four values at distinct wavelengths (full, quarter, half and three quarters). For incident vertical polarized light oriented at a 45 degree angle from the fast axis, the resultant retardations, $\delta(1)$ to $\delta(4)$ respectively, result in generated polarization states of vertical, right circular, horizontal and left circular, and are represented by the following Stokes parameter:

$$S_0 = I \quad \text{(Eq. 8a)}$$

$$S_1 = -I \cos \delta(i) \quad \text{(Eq. 8b)}$$

$$S_2 = 0 \quad \text{(Eq. 8c)}$$

$$S_3 = I \sin \delta(i) \quad \text{(Eq. 8d)}$$

Where i=1 to 4, and $\delta(i)$ can be represented by the following:

$$\delta(1) = 2\pi \Delta n(1) t/\lambda(1) = N2\pi \quad \text{(Eq. 9a)}$$

$$\delta(2) = 2\pi \Delta n(2) t/\lambda(2) = N2\pi + \pi/2 \quad \text{(Eq. 9b)}$$

$$\delta(3) = 2\pi \Delta n(3) t/\lambda(3) = N2\pi + \pi \quad \text{(Eq. 9c)}$$

$$\delta(4) = 2\pi \Delta n(4) t/\lambda(4) = N2\pi + 3\pi/2 \quad \text{(Eq. 9d)}$$

For a polarimeter having such a fixed waveplate 40, the four resultant generated polarization states are sufficient to make the measurements necessary to calculate seven out of the sixteen Mueller matrix elements containing both linear and circular characteristics (for example, $M_{00}$, $M_{01}$, $M_{03}$, $M_{10}$, $M_{30}$, $M_{11}$, and $M_{33}$). A fixed waveplate 40 in the analyzer portion of polarimeter 10 may convert circular polarization components back into linear polarization components in a quarter and three quarter waveplate and rotate linear components by 90 degrees in a half waveplate.

Figure 2:
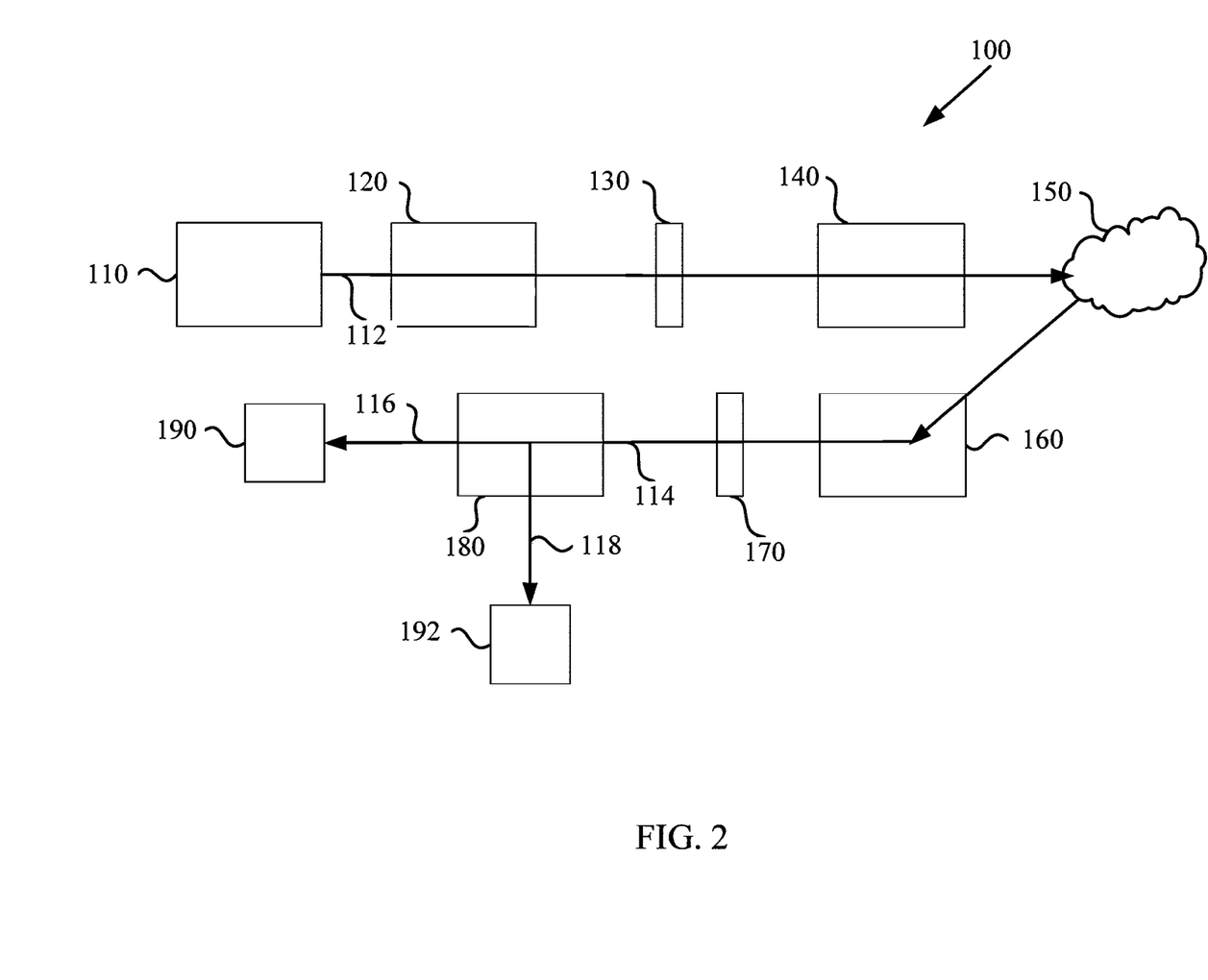
FIG. 2 shows a block diagram of an embodiment of a bi-static or transmission high-speed polarimeter having a multi-wavelength source.

Polarimeter 10 may include a fixed waveplate 40 on the generator path and another identical fixed waveplate on the analyzer path (for example, see FIG. 2). Fixed waveplate 40 may propagate radiation polarized along two orthogonal axes at different velocities. The axes may be oriented at a 45 degree angle from the orientation of the linear polarized radiation emitted by multi-wavelength source 20 and wave separator 30 in the plane perpendicular to the direction of propagation. The difference in velocity between the axes may depend on the wavelength of the radiation. The difference in velocity at a given wavelength and the thickness of fixed waveplate 40 may determine the phase difference between orthogonal axes. As an example, for a multi-wavelength source 20 generating an electromagnetic wave 22 having four wavelengths, at the first wavelength, w1, the phase difference is zero and the polarized state of radiation is unaffected by the waveplate. At the second wavelength, w2, the phase difference is 90 degrees and the generated radiation is circularly polarized. Orthogonal circular polarization components from the incoming beam are converted to orthogonal linear polarization components. At the third wavelength, w3, the phase difference is 180 degrees and the generated radiation is linear polarized orthogonal to the original orientation of the radiation incident on item 3. Orthogonal linear polarization components from the incoming beam are rotated by 90 degrees and are orthogonal linear polarization components. At the fourth wavelength, w4, the phase difference is 270 degrees and the generated radiation is circularly polarized, orthogonal to the sense generated by w2. The orthogonal circular polarization components from the incoming beam are converted to orthogonal linear polarization components.

Fixed waveplate 40 may serve to alter the polarization of an electromagnetic wave 22 passing through fixed waveplate 40. For example, in an embodiment of polarimeter 10 where multi-wavelength source 20 generates a continuous electromagnetic wave 22 sequentially having multiple wavelengths, with each wavelength having a single polarization, fixed waveplate 40 may serve to alter the polarization of electromagnetic wave 22 such that the resulting electromagnetic wave may have multiple polarizations, with each different wavelength having a different polarization. For example, for an electromagnetic wave 22 having four different wavelengths each having a vertical linear polarization prior to passing through fixed waveplate 40, the resulting electromagnetic wave may contain a wavelength having a vertical linear polarization, a wavelength having a horizontal linear polarization, a wavelength having a left circular polarization, and a wavelength having a right circular polarization.

In another embodiment wherein multi-wavelength source 20 may generate sequential pulsed electromagnetic waves each having a different wavelength, each pulse having a single polarization, fixed waveplate 40 may serve to alter the polarization of electromagnetic wave 22 such that the resulting electromagnetic wave may have multiple polarizations, with each different wavelength having a different polarization. For example, for an electromagnetic wave 22 having four separate pulses each having a different wavelength and a linear polarization prior to passing through fixed waveplate 40, the resulting electromagnetic wave may contain a pulse having a first wavelength and having a linear polarization, a pulse having a second wavelength and having a horizontal linear polarization, a pulse having a third wavelength and having a left circular polarization, and a pulse having a fourth wavelength and having a right circular polarization.

Free space coupler 50 may be operatively connected to fixed waveplate 40. Free space coupler 50 may serve to couple electromagnetic waves 22 generated from multi-wavelength source 20 into free space, towards sample 60. Free space coupler 50 may also couple the incoming electromagnetic waves from sample 60 to waveplate 40 and wave separator 30. An example of free space coupler 50 is a telescope comprised of two lenses for light radiation, which may be commercially obtained from Newport Corporation, Thorlabs, or New Focus Corporation. Beam splitter 70 may be operatively connected to wave separator 30. Beam splitter 70 may comprise an orthogonal polarization beam splitter. Beam splitter 70 may serve to direct each of the two orthogonal linear polarized components in the analyzer portion of polarimeter 10 to either detector 80 or detector 90. An example of a beam splitter 70 suitable for use with polarimeter 10 may be commercially obtained from Thorlabs, model PBS3.

Detectors 80 and 90 may be operatively connected to beam splitter 70. Detectors 80 and 90 may serve to measure the flux intensity of the electromagnetic waves received from sample 60. As an example, detector 80 may be configured to measure horizontal polarity intensity, while detector 90 may be configured to measure vertical polarity intensity, where:

$$H=0.5*[M00-\cos(\delta)M01+\sin(\delta)M03+\cos(\delta)M10+\sin(\delta)M30-\cos^2(\delta)M11-\sin(\delta)\cos(\delta)M31+\sin(\delta)\cos(\delta)M13+\sin^2(\delta)M33] \quad \text{(Eq. 10a)}$$

$$V=0.5*[M00-\cos(\delta)M01-\sin(\delta)M03-\cos(\delta)M10-\sin(\delta)M30+\cos^2(\delta)M11+\sin(\delta)\cos(\delta)M31-\sin(\delta)\cos(\delta)M13-\sin^2(\delta)M33] \quad \text{(Eq. 10b)}$$

If $\delta=0$, 90, 180 and 270 degrees for wavelengths 1-4 respectively, seven of the sixteen Mueller matrix elements may be calculated based on H(i) and V(i) measurements at all four wavelengths, i=1 to 4 using the following expressions:

$$M00=0.5*[H(1)+V(1)+H(3)+V(3)] \quad \text{(Eq.11a)}$$

$$M01=0.5*[-H(1)-V(1)+H(3)+V(3)] \quad \text{(Eq. 11b)}$$

$$M10=0.5*[H(1)-V(1)-H(3)+V(3)] \quad \text{(Eq.11c)}$$

$$M11=0.5*[-H(1)+V(1)-H(3)+V(3)] \quad \text{(Eq. 11d)}$$

$$M03=0.5*[+H(2)+V(2)-H(4)-V(4)] \quad \text{(Eq. 11e)}$$

$$M30=0.5*[H(2)-V(2)-H(4)+V(4)] \quad \text{(Eq. 11f)}$$

$$M33=0.5*[H(2)-V(2)+H(4)-V(4)] \quad \text{(Eq. 11g)}$$

In a monostatic configuration, wherein polarimeter 10 contains a single fixed waveplate 40 and a wave separator 30 for separating the incoming and outgoing electromagnetic waves, detectors 80 and 90 measure the horizontal and vertical components and the multi-wavelength source is vertically polarized. A similar set of measurements and calculations may be performed with different initial polarization states, waveplate and set of two detectors. In general, if multi-wavelength source 20 has polarization state defined by Stokes parameters S0, S1, S2 and S3, the resultant polarized waves incident on detectors 80 and 90 may be defined by S0', S1', S2' and S3' where $$S0'=S0M00-[S1\cos(\delta)+S3\sin(\delta)]M01+S2M02+[-S1\sin(\delta)+S3\cos(\delta)]M03 \quad \text{(Eq. 12a)}$$

$$S1'=S0\cos(\delta)M10+[S1\cos^2(\delta)+S3\cos(\delta)\sin(\delta)]M11+S2\cos(\delta)M12+[-S1\cos(\delta)\sin(\delta)+S3\cos^2(\delta)]M13+S0\sin(\delta)M30+[S1\cos(\delta)\sin(\delta)+S3\sin^2(\delta)]M31+S2\sin(\delta)M23+[-S1\sin^2(\delta)+S3\cos(\delta)\sin(\delta)]M33 \quad \text{(Eq. 12b)}$$

$$S2'=-S0M20-[S1\cos(\delta)+S3\sin(\delta)]M21-S2M22-[-S1\sin(\delta)+S3\cos(\delta)]M23 \quad \text{(Eq. 12c)}$$

$$S3'=S0\sin(\delta)M10+[S1\cos(\delta)\sin(\delta)+S3\sin^2(\delta)]M11+S2\sin(\delta)M12+[-S1\sin^2(\delta)+S3\cos(\delta)\sin(\delta)]M13-S0\cos(\delta)M30-[S1\cos^2(\delta)+S3\cos(\delta)\sin(\delta)]M31-S2\cos(\delta)M23-[-S1\cos(\delta)\sin(\delta)+S3\cos^2(\delta)]M33 \quad \text{(Eq. 12d)}$$

If detectors 80 and 90 are measuring horizontal and vertical components, H and V, the measured intensities may be represented by:

$$H=0.5*[S0'+S1'] \quad \text{(Eq. 13a)}$$

$$V=0.5*[S0'-S1'] \quad \text{(Eq. 13b)}$$

If detectors 80 and 90 are measuring right and left circular components, R and L, the measured intensities may be represented by:

$$R=0.5*[S0'+S3'] \quad \text{(Eq. 14a)}$$

$$L=0.5*[S0'-S3'] \quad \text{(Eq. 14b)}$$

Multiple configurations can be used to take the necessary measurements to calculate seven out of the sixteen Mueller matrix elements. Examples of detectors 80 and 90 that may be suitable for use with polarimeter 10 may be photodiodes commercially obtained from Newport Corporation, Thorlabs, New Focus, and cameras from FLIR/Indigo (Alpha InGaAs sensor for 1550 nm), or Cohu camera (for visible and near infrared wavelengths). Four detectors can be used to make the intensity measurements necessary to calculate all Stokes parameters in the analyzer. Coupled with a sequential source of four polarization states, the polarimeter can make the measurements necessary to calculate all 16 Mueller matrix elements at high-speed.

FIG. 2 shows a block diagram of another embodiment of the high-speed polarimeter having a multi-wavelength source 100. Polarimeter 100 may be configured in a bi-static or transmission mode, wherein polarimeter 100 may include a multi-wavelength source 110, a polarizer 120, a fixed waveplate 130, a transmitter free space coupler 140, a receiver free space coupler 160, a fixed waveplate 170, a beam splitter 180, and detectors 190 and 192. Multi-wavelength source 110 may create an electromagnetic wave 112 that is transmitted to polarizer 120, fixed waveplate 130, transmitter free space coupler 140, and to a sample 150. Polarizer 120 may be utilized with multi-wavelength sources 110 that do not contain polarizing elements. Thus, if multi-wavelength source 110 contains a polarizing element, polarizer 120 may be optional, depending on the type of polarization of electromagnetic wave 114 desired. Waveplate 130 may be optional if source 110 is comprised of multiple laser sources with each source having a unique polarization state.

The interaction of electromagnetic wave 112 with sample 150 may cause an electromagnetic wave 114 to be directed towards receiver free space coupler 160, fixed waveplate 170, and beam splitter 180. The polarization state of electromagnetic wave 114 may be the same as the electromagnetic wave 112, or it may be different, depending on the shape, angle, and surface material of sample 150. Sample 150 may comprise any type of material, in any shape or form. Beam splitter 180 may divide electromagnetic wave 114 into its horizontal and vertical components, horizontal component 116 and vertical component 118, which may then be directed to detectors 190 and 192. As an example, horizontal component 116 is directed to detector 190, which may be configured to detect horizontal components of electromagnetic waves, and vertical component 118 is directed to detector 192, which may be configured to detect vertical components of electromagnetic waves. In another embodiment, beam splitter 180 may also divide electromagnetic wave 114 into circular components, which then may be directed to detectors 190 and/or 192.

Multi-wavelength source 110 may be identical to multi-wavelength source 20. Fixed waveplate 130 and fixed waveplate 170 may be identical to fixed waveplate 40. Transmitter free space coupler 140 and receiver free space coupler 160 may be identical to free space coupler 50. Beam splitter 180 may be identical to beam splitter 70. Detectors 190 and 192 may be identical to detectors 80 and 90 respectively. An example of polarizer 120 is a linear polarizer, which may be commercially obtained from Thorlabs, CVI Corporation, and other sources. Polarimeter 100 may be used where it is desired to have separate generator and analyzer components, such that the generator component may be located on one end of a sample, such as sample 150, and the analyzer component may be located on the other end of the sample in transmission or bi-static reflection configuration.

Figure 3:
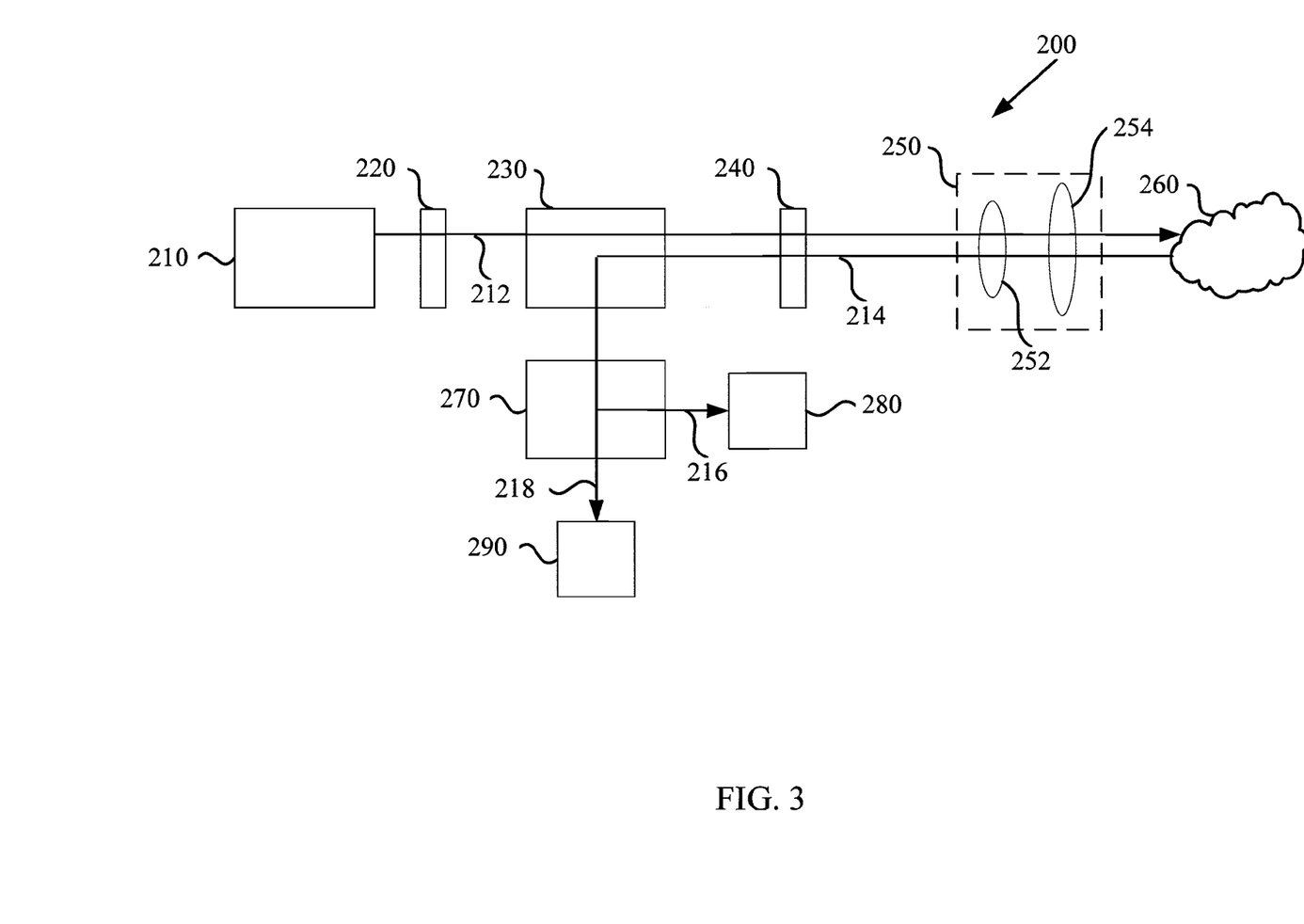
FIG. 3 shows a block diagram of an embodiment of a monostatic reflection mode high-speed polarimeter using a refractor telescope and having a multi-wavelength source.

FIG. 3 shows a block diagram of an embodiment of the high-speed polarimeter having a multi-wavelength source 200. Polarimeter 200 may have a monostatic reflective configuration, wherein polarimeter 200 may include a multi-wavelength source 210, a polarizer 220, an electromagnetic wave separator 230, a fixed waveplate 240, a telescope 250, a beam splitter 270, and detectors 280 and 290. Multi-wavelength source 210 may create an electromagnetic wave 212 that is transmitted to polarizer 220, wave separator 230, fixed waveplate 240, telescope 250, and to a sample 260. The interaction of electromagnetic wave 212 with sample 260 may cause an electromagnetic wave 214 to be redirected back towards telescope 250, fixed waveplate 240, and electromagnetic wave separator 230. The polarization state of electromagnetic wave 214 may be the same as the electromagnetic wave 212, or it may be different, depending on the shape, angle, and surface material of sample 260. Sample 260 may comprise any type of material, in any shape or form. At wave separator 230, electromagnetic wave 214 is directed to beam splitter 270. Beam splitter 270 may divide electromagnetic wave 214 into its horizontal and vertical components, horizontal component 216 and vertical component 218, which may then be directed to detectors 280 and 290. As an example, horizontal component 216 may be directed to detector 280, which may be configured to detect horizontal components of electromagnetic waves, and vertical component 218 may be directed to detector 290, which may be configured to detect vertical components of electromagnetic waves.

Multi-wavelength source 210 may be identical to multi-wavelength source 20. Polarizer 220 may be identical to polarizer 120. Wave separator 230 may be identical to wave separator 30. Fixed waveplate 240 may be identical to fixed waveplate 40. Beam splitter 270 may be identical to beam splitter 70. Detectors 280 and 290 may be identical to detectors 80 and 90 respectively. Telescope 250 may contain lenses 252 and 254 for providing refractive optic capabilities for beam expansion and divergence for remote detection polarimeters. An example of a refractor telescope 250 is a two lenses beam expander, which may be commercially obtained from Newport Corporation or Melles Griot. Polarimeter 200 may be utilized in applications involving remote detection of samples where beam expansion of electromagnetic waves is necessary to completely illuminate the sample at a distance and to collect the returning electromagnetic waves with a large aperture and reduce the size of the beam for analysis.

Figure 4:
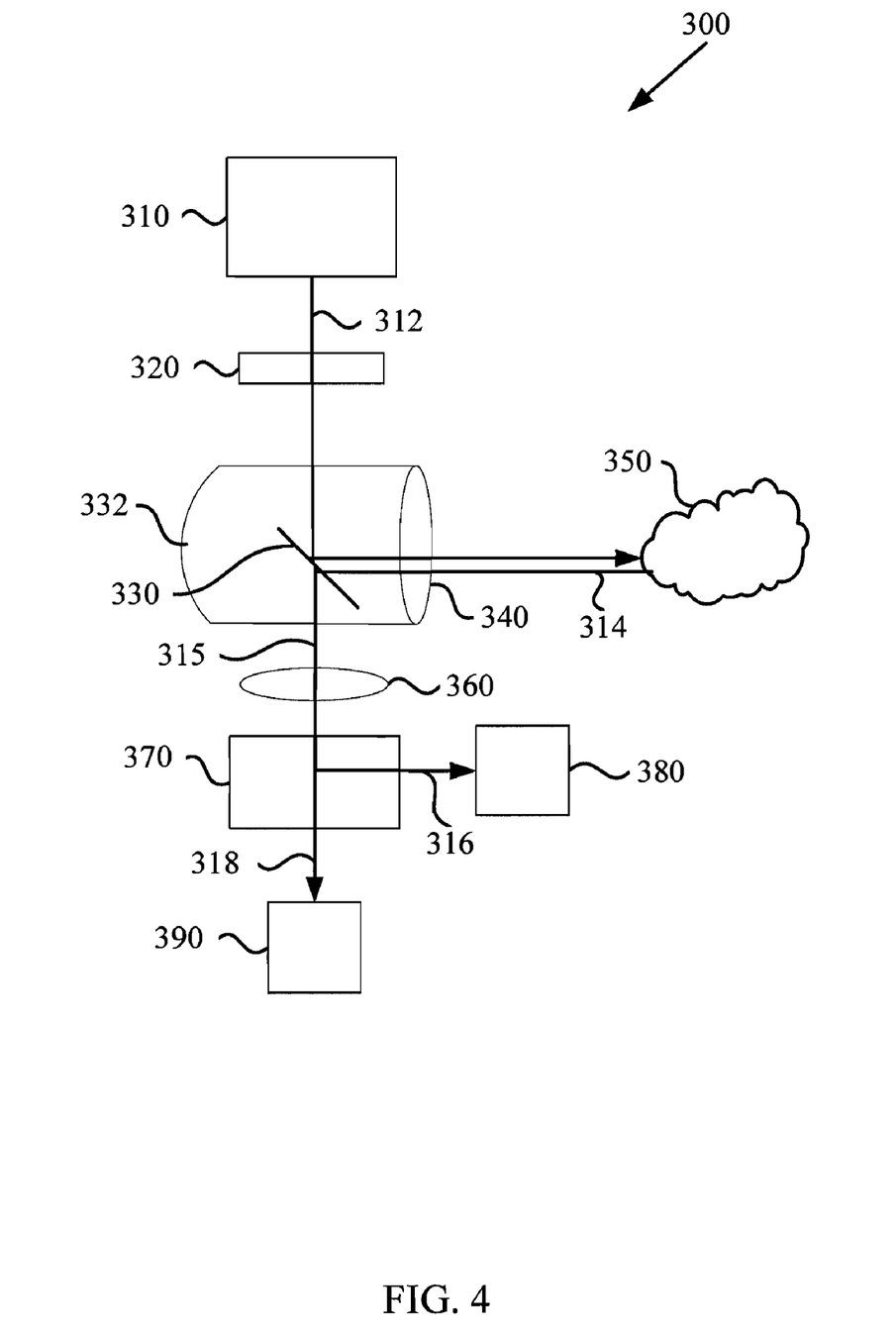
FIG. 4 shows a block diagram of an embodiment of a monostatic reflection mode high-speed polarimeter using a reflector telescope, a single waveplate, and having a multi-wavelength source.

FIG. 4 shows a block diagram of an embodiment of the high-speed polarimeter having a multi-wavelength source 300. Polarimeter 300 may have a monostatic reflective configuration, wherein polarimeter 300 may include a multi-wavelength source 310, a polarizer 320, a secondary mirror 330, a primary mirror 332, a fixed waveplate 340, a lens 360, a beam splitter 370, and detectors 380 and 390. Multi-wavelength source 310 may create an electromagnetic wave 312 that is transmitted to polarizer 320, the front side of secondary mirror 330, fixed waveplate 340, and to a sample 350. The interaction of electromagnetic wave 312 with sample 350 may cause an electromagnetic wave 314 to be directed towards primary mirror 332. The polarization state of electromagnetic wave 314 may be the same as the electromagnetic wave 312, or it may be different, depending on the shape, angle, and surface material of sample 350. Sample 350 may comprise any type of material, shaped in any form. Primary mirror 332 may then focus electromagnetic wave 314 onto the back side of secondary mirror 330, causing electromagnetic wave 315 to be directed towards lens 360 and beam splitter 370. Lens 360 may serve to collimate the electromagnetic wave energy into beam splitter 370. Beam splitter 370 may divide electromagnetic wave 314 into its horizontal and vertical components, horizontal component 316 and vertical component 318, which are then directed to detectors 380 and 390. As an example, horizontal component 316 may be directed to detector 380, which may be configured to detect horizontal components of electromagnetic waves, and vertical component 318 may be directed to detector 390, which may be configured to detect vertical components of electromagnetic waves.

Multi-wavelength source 310 may be identical to multi-wavelength source 20. Polarizer 320 may be identical to polarizer 120. Fixed waveplate 340 may be identical to fixed waveplate 40. Beam splitter 370 may be identical to beam splitter 70. Detectors 380 and 390 may be identical to detectors 80 and 90 respectively. An example of secondary mirror 330 is a flat mirror, which may be commercially obtained from Melles Griot or CVI Corporation. An example of primary mirror 332 is a parabolic mirror, which may be commercially obtained from Meade. In one embodiment, secondary mirror 330 and primary mirror 332 may comprise a "Newtonian telescope." An example of lens 360 is a 10 mm biconvex lens, which may be commercially obtained from Newport Corporation.

Figure 5:
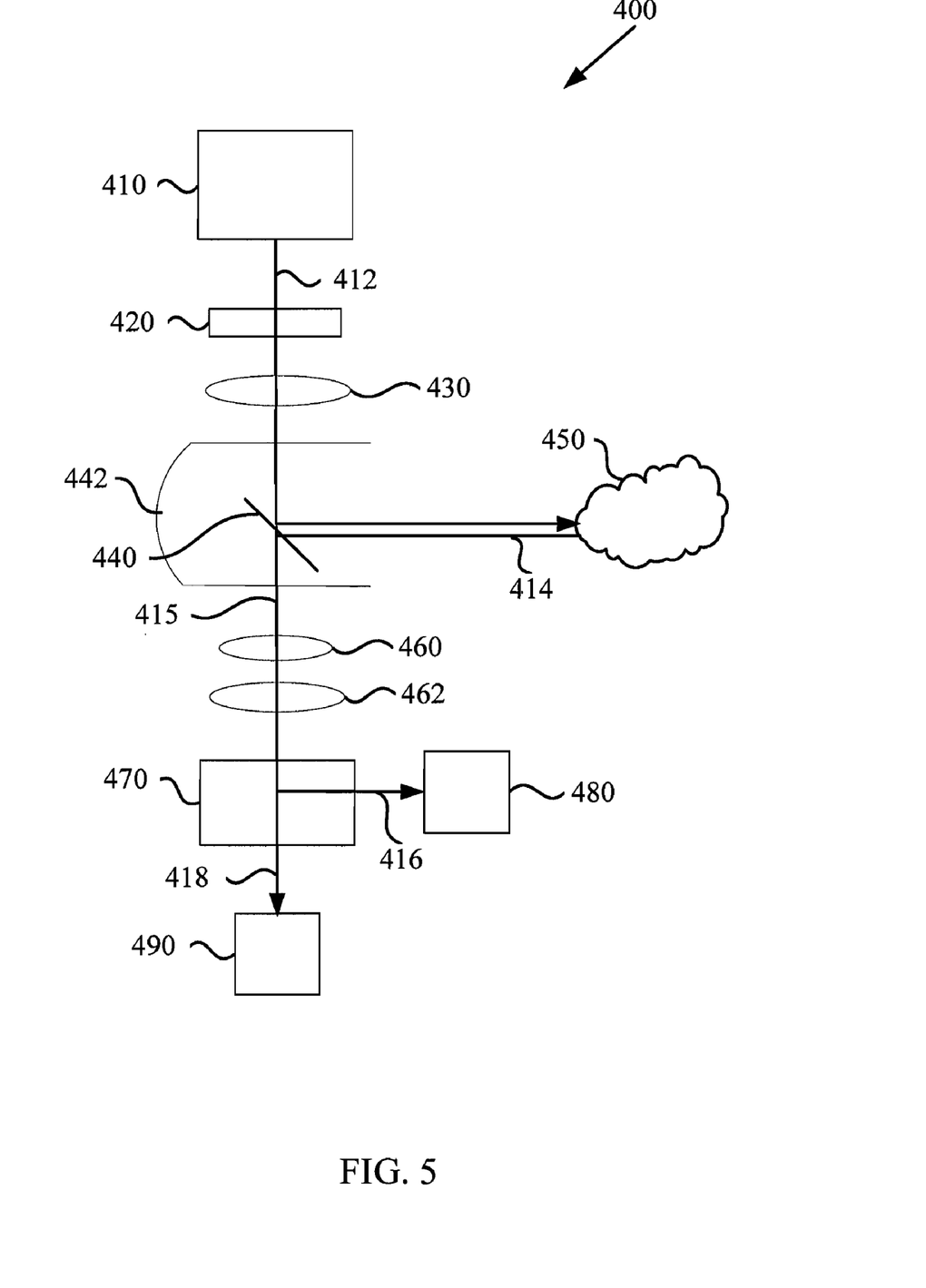
FIG. 5 shows a block diagram of an embodiment of a monostatic reflection mode high-speed polarimeter using a reflector telescope and having a multi-wavelength source.

FIG. 5 shows a block diagram of an embodiment of the high-speed polarimeter having a multi-wavelength source 400. Polarimeter 400 may have a monostatic reflective configuration, wherein polarimeter 400 may include a multi-wavelength source 410, a polarizer 420, a fixed waveplate 430, a secondary mirror 440, a primary mirror 442, a lens 460, a fixed waveplate 462, a beam splitter 470, and detectors 480 and 490. Multi-wavelength source 410 may create an electromagnetic wave 412 that is transmitted to polarizer 420, fixed waveplate 430, the front side of secondary mirror 440, and to a sample 450. Fixed waveplate 430 may serve to convert different wavelengths into different polarizing states. Waveplate 430 may be optional if source 410 is comprised of multiple laser sources with each source having a unique polarization state.

The interaction of electromagnetic wave 412 with sample 450 may cause an electromagnetic wave 414 to be directed towards primary mirror 442. The polarization state of electromagnetic wave 414 may be the same as the electromagnetic wave 412, or it may be different, depending on the shape, angle, and surface material of sample 450. Sample 450 may comprise any type of material, shaped in any form. Primary mirror 442 may then focus electromagnetic wave 414 onto the back side of secondary mirror 440, causing electromagnetic wave 415 to be directed towards lens 460, fixed waveplate 462, and beam splitter 470. Lens 460 may serve to collimate electromagnetic waves into waveplate 462. Fixed waveplate 462 may serve to convert received electromagnetic waves to different polarization states based on wavelengths. Beam splitter 470 may divide electromagnetic wave 415 into its horizontal and vertical components, horizontal component 416 and vertical component 418, which are then directed to detectors 480 and 490. As an example, horizontal component 416 may be directed to detector 480, which may be configured to detect horizontal components of electromagnetic waves, and vertical component 418 may be directed to detector 490, which may be configured to detect vertical components of electromagnetic waves.

Multi-wavelength source 410 may be identical to multi-wavelength source 20. Polarizer 420 may be identical to polarizer 120. Fixed waveplate 430 may be identical to fixed waveplate 40. Secondary mirror 440 may be identical to secondary mirror 330. Primary mirror 442 may be identical to primary mirror 332. Lens 460 may be identical to lens 360. Fixed waveplate 462 may be identical to fixed waveplate 40. Beam splitter 470 may be identical to beam splitter 70. Detectors 480 and 490 may be identical to detectors 80 and 90 respectively. Polarimeter 400 may be used where it is desired to have a fixed waveplate smaller than the primary mirror due to cost, size and weight.

Figure 6:
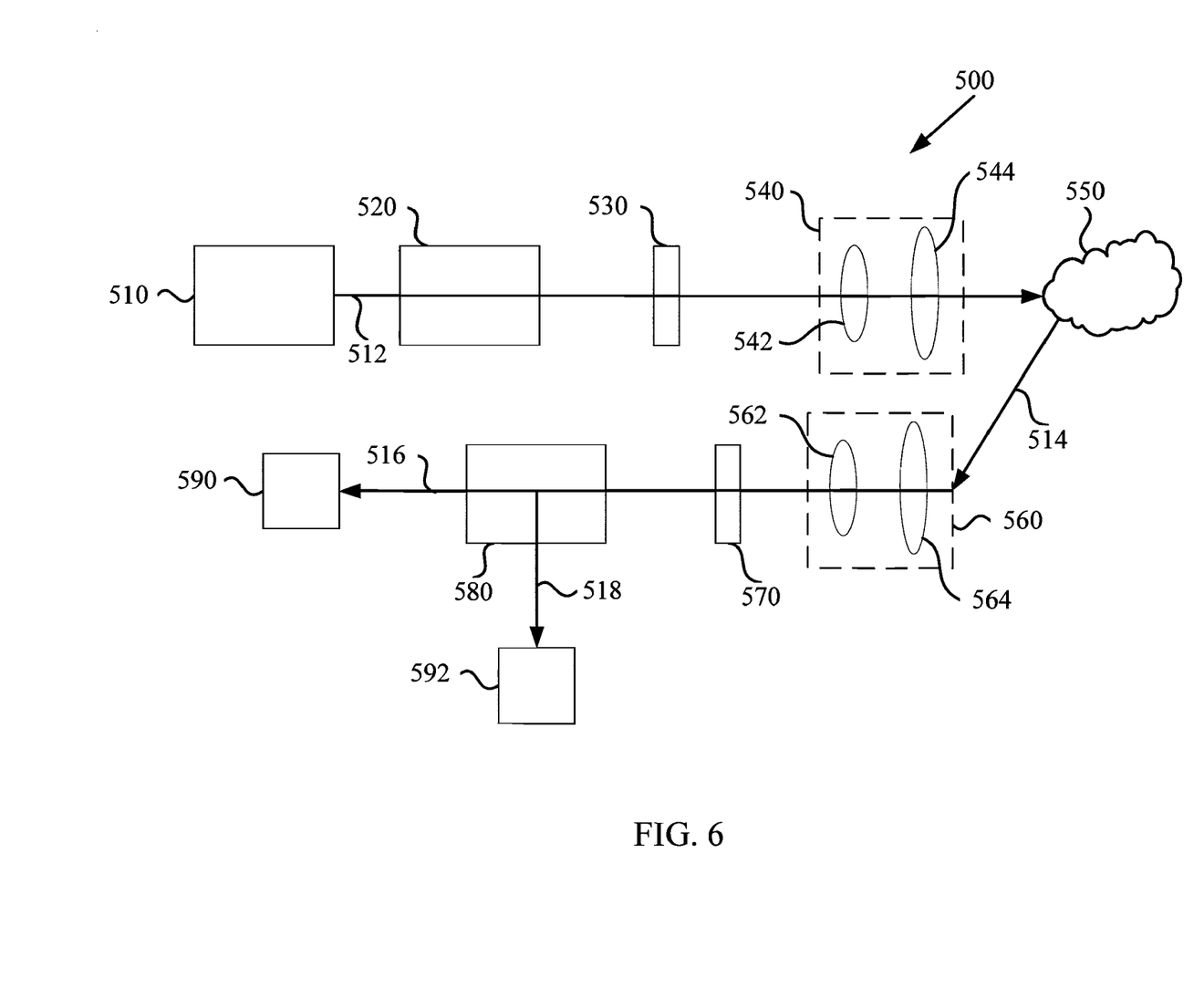
FIG. 6 shows a block diagram of an embodiment of a bi-static or transmission high-speed polarimeter using a telescope and having a multi-wavelength source.

FIG. 6 shows a block diagram of an embodiment of the high-speed polarimeter having a multi-wavelength source 500. Polarimeter 500 may have a bi-static or transmission configuration, wherein polarimeter 500 may include a multi-wavelength source 510, a polarizer 520, a fixed waveplate 530, a transmitter telescope 540, a receiver telescope 560, a fixed waveplate 570, a beam splitter 580, and detectors 590 and 592. Multi-wavelength source 510 may create an electromagnetic wave 512 that is transmitted to polarizer 520, fixed waveplate 530, transmitter telescope 540, and to a sample 550. Polarizer 520 may be utilized with multi-wavelength sources 510 that do not contain polarizing elements. Thus, if multi-wavelength source 510 contains a polarizing element, polarizer 520 may be optional, depending on the type of polarization of electromagnetic wave 512 desired. Waveplate 530 may be optional if source 510 is comprised of multiple laser sources with each source having a unique polarization state.

The interaction of electromagnetic wave 512 with sample 550 may cause an electromagnetic wave 514 to be directed towards receiver telescope 560, fixed waveplate 570, and beam splitter 580. The polarization state of electromagnetic wave 514 may be the same as the electromagnetic wave 512, or it may be different, depending on the shape, angle, and surface material of sample 550. Sample 550 may comprise any type of material, shaped in any form. Beam splitter 580 may divide electromagnetic wave 514 into its horizontal and vertical components, horizontal component 516 and vertical component 518, which are then directed to detectors 590 and 592. As an example, horizontal component 516 may be directed to detector 590, which may be configured to detect horizontal components of electromagnetic waves, and vertical component 518 is directed to detector 592, which may be configured to detect vertical components of electromagnetic waves.

Multi-wavelength source 510 may be identical to multi-wavelength source 20. Polarizer 520 may be identical to polarizer 120. Fixed waveplate 530 and fixed waveplate 570 may be identical to fixed waveplate 40. Beam splitter 580 may be identical to beam splitter 70. Detectors 590 and 592 may be identical to detectors 80 and 90 respectively. Transmitter telescope 540 may contain lenses 542 and 544. Transmitter telescope 540 may be identical to telescope 250. Receiver telescope 560 may contain lenses 562 and 564. Receiver telescope 560 may be identical to telescope 250. Polarimeter 500 may be used where it is desired to have transmission measurements or bi-static reflection measurements where the electromagnetic waves need to be expanded on to the sample, as well as when it is desired to have separate generator and analyzer components, such that the generator component may be located on one end of a sample, such as sample 550, and the analyzer component may be located on the other end of the sample.

Figure 7:
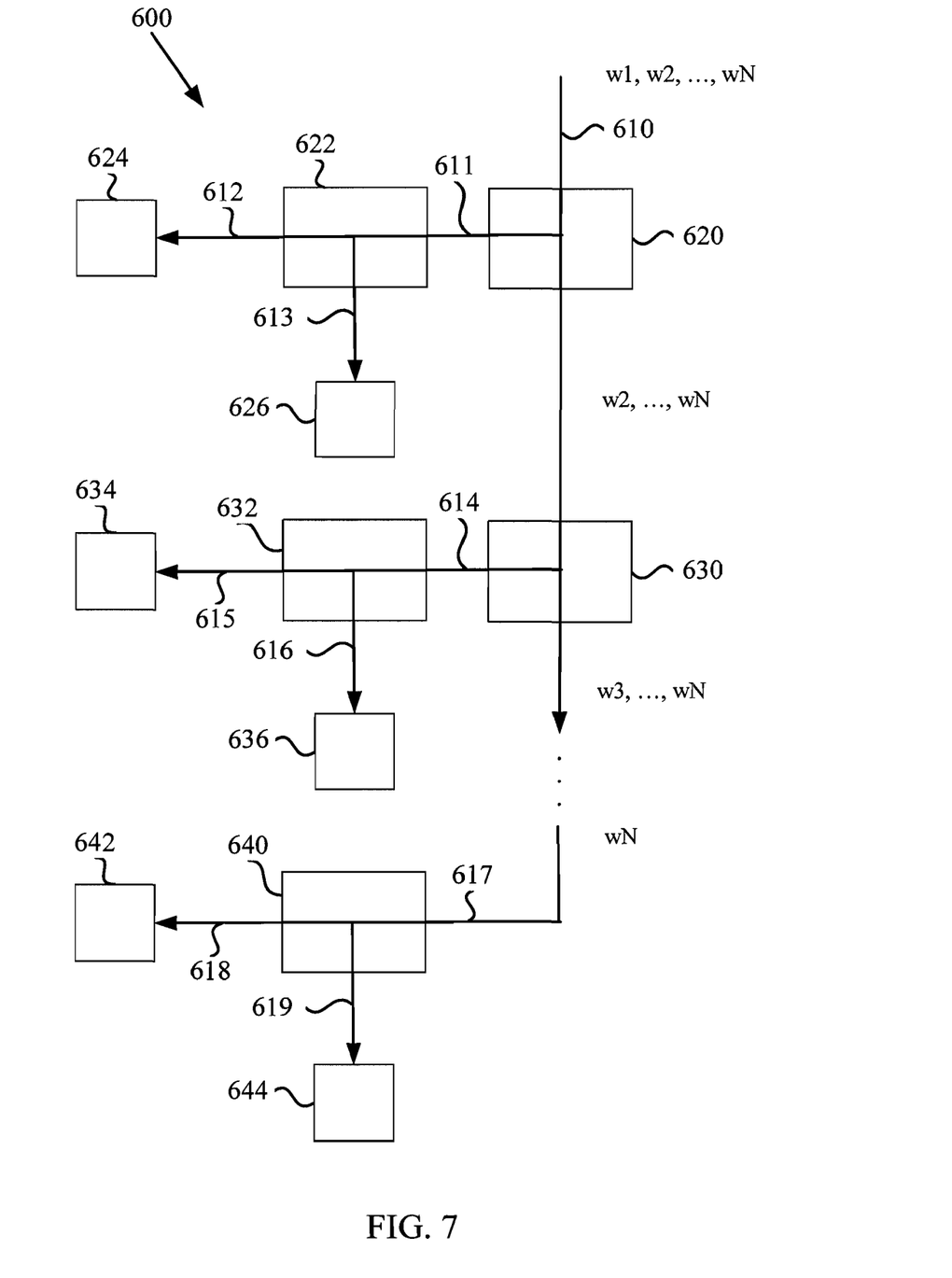
FIG. 7 shows a block diagram of a portion of an embodiment of a high-speed polarimeter using a wavelength division coupler, having a multi-wavelength source, and having two detectors for each wavelength.

FIG. 7 shows a block diagram of a portion of an embodiment of the high-speed polarimeter having a multi-wavelength source 600. Polarimeter 600 may contain a multi-wavelength source, polarizing elements for each wavelength, a wave separator, and one or more free space couplers (components not shown), for the transmission of an electromagnetic wave to a sample (not shown) and to receive an electromagnetic wave from the sample. Polarimeter 600 may allow for simultaneous measurement of linear and circular components, allowing the subsequent calculation of seven Mueller matrix elements. The source may be continuous or pulsed simultaneously at different wavelengths. A received electromagnetic wave 610 may have multiple wavelengths, w1, w2, . . . , wN. Electromagnetic wave 610 may be directed to a wavelength division coupler 620. Wavelength division coupler 620 may serve to separate a wavelength from electromagnetic wave 610, direct an electromagnetic wave having the separate wavelength to beam splitter 622, and to direct electromagnetic wave 610, having one less wavelength, to another wavelength division coupler, such as wavelength division coupler 630. Multiple wavelength division couplers may be employed within polarimeter 600, from 1 to N−1, depending on the number of wavelengths, N, of electromagnetic wave 610 that are to be separated. An example of a wavelength division coupler suitable for use with polarimeter 600 may be commercially obtained from bulk dichroic filters from CVI Corporation or fiber DWDM couplers from OptiWorks.

Beam splitter 622 may divide electromagnetic wave 611 into its horizontal and vertical components, horizontal component 612 and vertical component 613, which are then directed to detectors 624 and 626. As an example, horizontal component 612 may be directed to detector 624, which may be configured to detect horizontal components of electromagnetic waves, and vertical component 613 may be directed to detector 626, which may be configured to detect vertical components of electromagnetic waves.

As an example of the operation of the wavelength division couplers, if electromagnetic wave 610 contains wavelengths w1, w2, w3, and w4, wavelength division coupler 620 may serve to separate w1 from electromagnetic wave 610, direct electromagnetic wave 611, having a wavelength equal to w1, to beam splitter 622, and direct electromagnetic wave 610, having wavelengths w2, w3, and w4, to wavelength division coupler 630. Wavelength division coupler 630 may serve to separate a wavelength from electromagnetic wave 610, direct an electromagnetic wave having the separate wavelength to beam splitter 632, and to direct electromagnetic wave 610, having one less wavelength, to another wavelength division coupler (not shown). For example, if electromagnetic wave 610 contains wavelengths w2, w3, and w4, wavelength division coupler 630 may serve to separate w2 from electromagnetic wave 610, direct electromagnetic wave 614, having a wavelength equal to w2, to beam splitter 632, and direct electromagnetic wave 610, having wavelengths w3, and w4, to another wavelength division coupler (not shown). Wavelength division coupler 630 may be similar to wavelength division coupler 620, varying only in the structure required to separate a different wavelength from electromagnetic wave 610.

Beam splitter 632 may divide electromagnetic wave 614 into its horizontal and vertical components, horizontal component 615 and vertical component 616, which are then directed to detectors 634 and 636. As an example, horizontal component 615 may be directed to detector 634, which may be configured to detect horizontal components of electromagnetic waves, and vertical component 616 may be directed to detector 636, which may be configured to detect vertical components of electromagnetic waves.

From wavelength division coupler 630, electromagnetic wave 610 may be directed to various wavelength division couplers within polarimeter 600. After passing through the last wavelength division coupler, the corresponding electromagnetic wave, shown as electromagnetic wave 617, may be directed to beam splitter 640. Electromagnetic wave 617 may have a wavelength wN. Beam splitter 640 may divide electromagnetic wave 617 into its horizontal and vertical components, horizontal component 618 and vertical component 619, which are then directed to detectors 642 and 644. As an example, horizontal component 618 may be directed to detector 642, which may be configured to detect horizontal components of electromagnetic waves, and vertical component 619 may be directed to detector 644, which may be configured to detect vertical components of electromagnetic waves.

Figure 8:
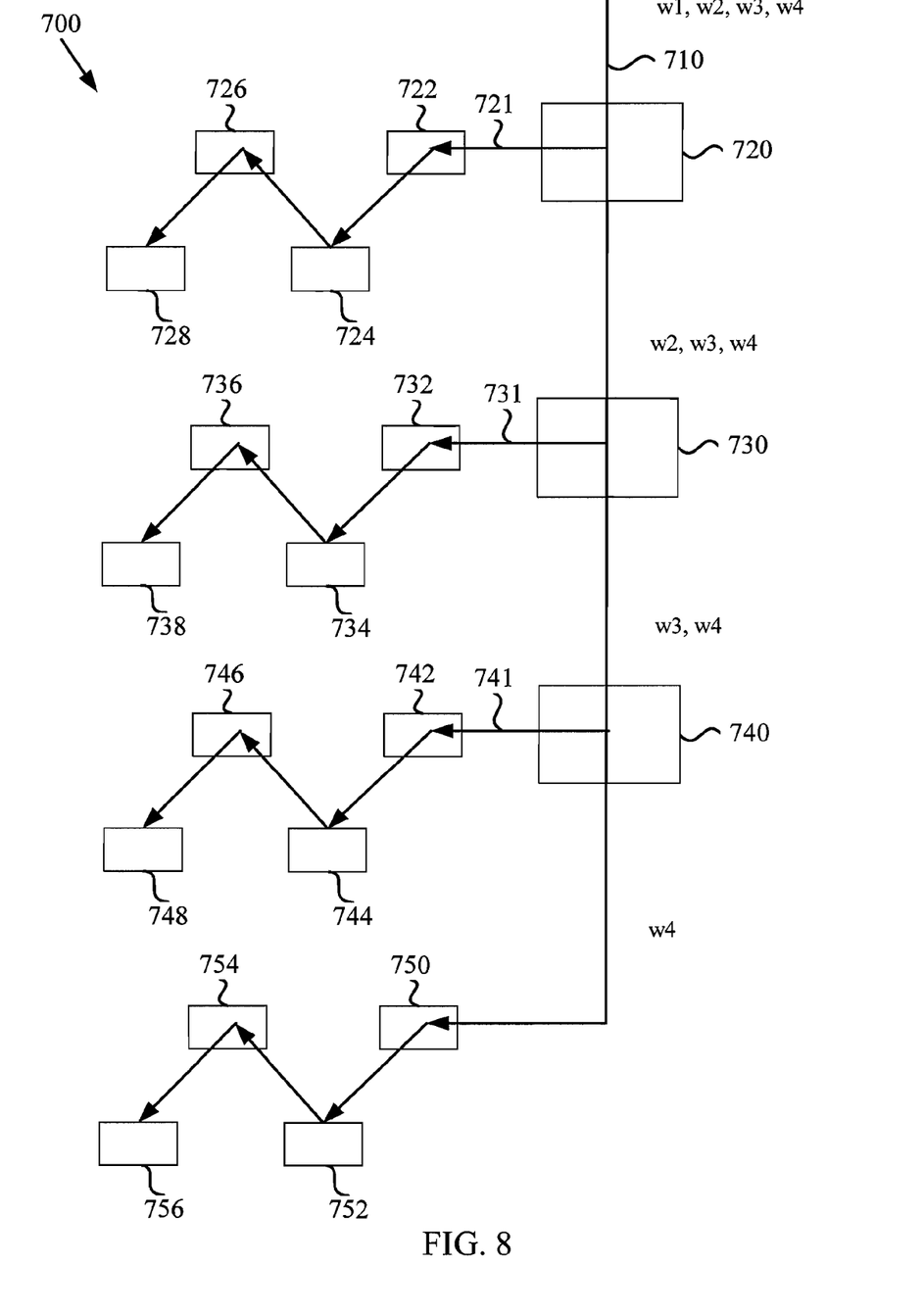
FIG. 8 shows a block diagram of a portion of an embodiment of a high-speed polarimeter using a wavelength division coupler, a multi-wavelength source, and having four detectors for each wavelength.

FIG. 8 shows a block diagram of a portion of an embodiment of the high-speed polarimeter having a multi-wavelength source 700. Polarimeter 700 may contain a multi-wavelength source, polarizing elements for each wavelength, a wave separator, and one or more free space couplers (components not shown), for the transmission of an electromagnetic wave to a sample (not shown) and to receive an electromagnetic wave from the sample. Polarimeter 700 may allow for simultaneous measurement of linear and circular components, allowing for the subsequent simultaneous calculation of all sixteen Mueller matrix elements. The source may be continuous or simultaneously pulsed. A received electromagnetic wave 710 may have multiple wavelengths, w1, w2, . . . , wN. Electromagnetic wave 710 may be directed to a wavelength division coupler 720. Wavelength division coupler 720 may serve to separate a wavelength from electromagnetic wave 710, direct an electromagnetic wave 721 having the separate wavelength to detector 722, and to direct electromagnetic wave 710, having one less wavelength, to another wavelength division coupler, such as wavelength division coupler 730. Multiple wavelength division couplers may be employed within polarimeter 700, from 1 to N−1, depending on the number of wavelengths, N, of electromagnetic wave 710 that are to be separated. The wavelength division couplers utilized in polarimeter 700 may be identical to the wavelength division couplers utilized in polarimeter 600.

As an example of the operation of the wavelength division couplers, if electromagnetic wave 710 contains wavelengths w1, w2, w3, and w4, wavelength division coupler 720 may serve to separate w1 from electromagnetic wave 710, direct electromagnetic wave 721, having a wavelength equal to w1, to detector 722, and direct electromagnetic wave 710, having wavelengths w2, w3, and w4, to wavelength division coupler 730. From detector 722, electromagnetic wave 721 may be directed to an array of detectors, such as detectors 724, 726, and 728. Detectors 722, 724, 726, and 728 may each be configured to make the intensity measurements of electromagnetic wave 721 to allow for the calculation of the four Stokes parameters.

Wavelength division coupler 730 may serve to separate w2 from electromagnetic wave 710, direct an electromagnetic wave 731 having a wavelength of w2 to detector 732, and to direct electromagnetic wave 710, having wavelengths w3 and w4, to wavelength division coupler 740. From detector 732, electromagnetic wave 731 may be directed to an array of detectors, such as detectors 734, 736, and 738. Detectors 732, 734, 736, and 738 may each be configured to make the intensity measurements of electromagnetic wave 731 to allow for the calculation of the four Stokes parameters. Wavelength division coupler 740 may serve to separate w3 from electromagnetic wave 710, direct electromagnetic wave 741, having a wavelength equal to w3, to detector 742, and direct electromagnetic wave 710, having wavelength w4 to detector 750. From detector 742, electromagnetic wave 741 may be directed to an array of detectors, such as detectors 744, 746, and 748. Detectors 742, 744, 746, and 748 may each be configured to make the intensity measurements of electromagnetic wave 741 to allow for the calculation of the four Stokes parameters. From detector 750, electromagnetic wave 710 may be directed to an array of detectors, such as detectors 752, 754, and 756. Detectors 750, 752, 754, and 756 may each be configured to make intensity measurement of electromagnetic wave 710 to allow for the calculation of the four Stokes parameters.

The use of a multi-wavelength source allows for the simultaneous production of all necessary polarization components without the need to change optical components. This allows for the measurement of at least seven out of the sixteen Mueller Matrix elements needed to identify many of the linear and circular polarization characteristic of sample, including both linear and circular depolarization. Multiple wavelengths are used to speed up the measurement process by sequentially or simultaneously generating four polarization states. Further, the orthogonal components do not need to be "switched" in time with active electro-optical control of a variable retarder to provide separate orthogonal components. Each orthogonal component has a separate wavelength associated with it. Each wavelength has a separate amplitude and frequency modulation. Each wavelength and associated polarization component has a separate phase modulation after passing through fixed waveplate 40. As a result, polarimeters 10, 100, 200, 300, 400, 500, 600, and 700 have many applications. For example, the polarimeters may be used in measurements where fast variable samples and/or medium require the need for a high-speed device, such as in quality control for manufacturing lines and remote detection where large numbers of measurements are sampled in a scanning configuration. For example, scanning the surface of the earth from a moving platform with a monostatic polarimeter mounted on the platform where the polarimeter measures both linear and circular depolarization. A polarimeter configuration incorporating two wavelengths may be used to determine both linear and circular co-polarized and cross-polarized components. While this may not be sufficient to precisely determine Mueller matrix elements, it may be adequate to approximate the linear and circular depolarization characteristics of a sample. For samples and/or medium with little wavelength dependence within the set of multiple wavelengths used, the calculated values of both linear and circular depolarization and diattenuation may be approximated by the embodiments disclosed herein.

The scope of the claims is not limited to the embodiments disclosed herein, but extends to other embodiments as may be contemplated by those with ordinary skill in the art.

We claim:

1. A polarimeter comprising:
   a multi-wavelength source for generating electromagnetic waves having at least two different wavelengths and one polarization state;
   a first fixed waveplate operatively connected to the multi-wavelength source;
   a Newtonian telescope comprising a primary mirror and a secondary mirror, operatively connected to the first fixed waveplate;
   a lens operatively connected to the Newtonian telescope;
   a second fixed waveplate operatively connected to the lens;
   a beam splitter operatively connected to the second fixed waveplate; and
   more than one detector operatively connected to the beam splitter.

2. The polarimeter of claim 1, wherein the first fixed waveplate is configured to convert the one polarization state to multiple polarization states, a different polarization state for each wavelength, that allow for calculations of linear polarization components and circular polarization components of the electromagnetic waves.

3. The polarimeter of claim 1, wherein the multi-wavelength source comprises a pulsed source that periodically emits electromagnetic waves having different wavelengths.

4. The polarimeter of claim 1, wherein the multi-wavelength source comprises two or more sources combined with a coupling device, wherein each of the two or more sources operate at different wavelengths and the coupling device co-aligns the two or more sources such that the electromagnetic waves generated by each of the two or more sources pass through the means for separating electromagnetic waves.

5. The polarimeter of claim 4, wherein the two or more sources generate simultaneous electromagnetic waves having different wavelengths.

6. The polarimeter of claim 1, wherein the multi-wavelength source includes multiple pulsed sources, each pulsed source generating electromagnetic waves having different wavelengths, wherein each pulsed source sequentially emits radiation such that no two pulsed sources simultaneously emit radiation.

7. The polarimeter of claim 1, wherein the multi-wavelength source includes multiple pulsed sources, each pulsed source generating electromagnetic waves having different wavelengths, wherein each pulsed source simultaneously emits radiation with the other pulsed sources.

8. The polarimeter of claim 1, wherein the beam splitter comprises a plurality of orthogonal polarization beam splitters, each of the orthogonal polarization beam splitters coupled to at least two detectors, wherein each of the orthogonal polarization beam splitters receives an electromagnetic wave from the multi-wavelength source, each of the electromagnetic waves having a different wavelength, and transmits the electromagnetic wave to the at least two detectors.

9. The polarimeter of claim 1 further comprising a linear polarizer positioned between the multi-wavelength source and the first fixed waveplate.

10. The polarimeter of claim 1, wherein the more than one detector are each photodiodes.

11. The polarimeter of claim 1, wherein the more than one detector comprises an array of detector elements.

* * * * *